United States Patent
Plowiecki et al.

(10) Patent No.: US 9,968,470 B2
(45) Date of Patent: May 15, 2018

(54) STENT FOR BIFURCATION, A SYSTEM FOR INTRAVASCULAR IMPLANTATION OF THE STENT FOR BIFURCATION AND A METHOD OF IMPLANTATION OF THE STENT FOR BIFURCATION

(71) Applicant: BALTON Sp. z o.o., Warsaw (PL)

(72) Inventors: Emil Plowiecki, Warsaw (PL); Leszek Hurkala, Warsaw (PL)

(73) Assignee: BALTON SP. Z O.O. (PL)

( * ) Notice: Subject to any disclaimer, the term of this patent is extended or adjusted under 35 U.S.C. 154(b) by 686 days.

(21) Appl. No.: 14/316,899

(22) Filed: Jun. 27, 2014

(65) Prior Publication Data

US 2015/0039073 A1     Feb. 5, 2015

Related U.S. Application Data

(62) Division of application No. 13/558,740, filed on Jul. 26, 2012, now abandoned.

(30) Foreign Application Priority Data

Jun. 19, 2012 (PL) .......................... 399580

(51) Int. Cl.
| | |
|---|---|
| *A61F 2/82* | (2013.01) |
| *A61F 2/856* | (2013.01) |
| *A61F 2/915* | (2013.01) |
| *A61F 2/954* | (2013.01) |
| *A61F 2/958* | (2013.01) |
| *A61F 2/06* | (2013.01) |

(52) U.S. Cl.
CPC .............. *A61F 2/856* (2013.01); *A61F 2/915* (2013.01); *A61F 2/954* (2013.01); *A61F 2/958* (2013.01); *A61F 2002/061* (2013.01); *A61F 2002/828* (2013.01); *A61F 2002/91541* (2013.01); *A61F 2002/91575* (2013.01); *A61F 2250/0039* (2013.01); *A61F 2250/0098* (2013.01)

(58) Field of Classification Search
CPC ....................................................... A61F 2/82
See application file for complete search history.

(56) References Cited

U.S. PATENT DOCUMENTS

| | | | |
|---|---|---|---|
| 2004/0215326 A1 | 10/2004 | Goodson et al. | 623/1.16 |
| 2006/0206188 A1 | 9/2006 | Weber et al. | 623/1.11 |
| 2007/0203571 A1 | 8/2007 | Kaplan et al. | 613/1.16 |

FOREIGN PATENT DOCUMENTS

| | | |
|---|---|---|
| EP | 0 904 745 | 3/1999 |
| PL | 387865 | 10/2010 |
| WO | WO 01/74273 A1 | 10/2001 |
| WO | WO 2010/123387 | 10/2010 |

OTHER PUBLICATIONS

Polish Search Report dated Sep. 3, 2012.

*Primary Examiner* — Matthew Schall
(74) *Attorney, Agent, or Firm* — Ostrolenk Faber LLP

(57) ABSTRACT

A stent for bifurcation, including two cylindrical parts: a distal part (1.1) of smaller diameter and a proximal part (1.2) of greater diameter, connected by two arranged as opposite longitudinal connectors (1.3) having length (L1) of 0.5 to 8 mm and forming a cell of the stent having an enlarged surface area (1.4), the connectors having a curvilinear shape, in particular a sinusoidal shape. A method of introducing the stent and a system for intravascular implantation are disclosed.

20 Claims, 3 Drawing Sheets

STENT FOR BIFURCATION, A SYSTEM FOR INTRAVASCULAR IMPLANTATION OF THE STENT FOR BIFURCATION AND A METHOD OF IMPLANTATION OF THE STENT FOR BIFURCATION

The present application is a divisional under 37 C.F.R. § 1.53(b) of, and claims priority to, prior U.S. patent application Ser. No. 13/558,740, filed Jul. 26, 2012, which claims priority to Polish Patent Application No. P.399580, filed Jun. 19, 2012 by Emil Plowiecki and Leszek Hurkala entitled STENT FOR BIFURCATION, A SYSTEM FOR INTRAVASCULAR IMPLANTATION OF THE STENT FOR BIFURCATION AND A METHOD OF IMPLANTATION OF THE STENT FOR BIFURCATION, the entire content of the applications is incorporated by reference.

BACKGROUND OF THE INVENTION

Technical Field

Object of the invention is a stent for bifurcation, a system for intravascular implantation of the stent for bifurcation and a method of implantation of the stent for bifurcation.

Related Art

The state-of-the art systems for intravascular implantation of stent for bifurcation, utilizing various structural solutions at implantation of the stent, often bring about injuries, especially at ramifications of arteries. The most frequent problems at implantation of the stent for bifurcation include partial or complete closure of a lateral branch of arteries, contraction of lateral branch of artery, dissection at bifurcation of vessels, a decrease in a cross section of a lateral branch of artery as a result of covering of lumen with struts of an implanted stent, and occurrence of thrombosis foci.

To avoid such situations, at present either one stent per each branch is implanted while using separate systems for intravascular implantation for each of the implanted stents or one forked stent, mounted on the complicated system, is implanted.

Operations of intravascular implantation of stents for bifurcation using state-of-the-art methods are extremely complicated to implement and burdened with very high probability of various post-operational complications in arteries with stents. They must be carried out in surgeries provided with very modern equipment. Furthermore, operators carrying out the implantation are required to have high skills and much experience.

Accordingly, there is a demand for new, more effective structural solutions for stents for bifurcation and systems for intravascular implantation of such stents, in order to facilitate implantation at a bifurcation site even by less experienced operators and to provide higher safety and efficacy of operation.

Aim of the present invention, is to increase efficacy and to facilitate implantation procedure, thus increasing safety of operation and promoting more wide use of stents and developing more universal construction of stent extendable on a balloon, which allows its implantation in vessels having different shapes and sizes and of different mutual arrangement of a branch with respect to the main vessel.

From international application WO0174273A1 a self-extending stent made of materials, such as e.g., nickel and titanium alloys, consisting of two segments—proximal and distal is known, one of them having greater diameter, and the segments being connected by at least one longitudinal connector. That connector (or several connectors located close to each other) is rectilinear and is located only at one side of the stent, so that at the other side between two segments of the stent a free space is formed. The connector of the stent upon implanting in blood vessel adheres to an internal wall of the vessel and it bends in such a way that segments of the stent change their mutual position (there is an angle between them), and free space between them is freely increased.

SUMMARY OF THE INVENTION

A stent for bifurcation of the invention, consists of two cylindrical parts: a distal part of smaller diameter and a proximal part of greater diameter, connected by two—arranged as opposite—longitudinal connectors having length of 0.5 to 8 mm, that form a cell of the stent having an enlarged surface area, the connectors having a curvilinear shape, in particular a sinusoidal shape.

Preferably, a ratio of the distal part diameter to the proximal part diameter of the stent is within the limits of 1.0:1.1 to 1.0:2.0.

A system for intravascular implantation of the stent for bifurcation, consisting of the proximal part and the distal part including an external tube, an internal tube, and a profiled balloon, according to the invention, is characterized in that—in the distal part of the system—on the internal tube marked with three rings, visible at X-rays, there is a profiled balloon fastened with the proximal part to the external surface of the external tube and with the distal part—to the external surface of the internal tube, and on the profiled balloon, a stent for bifurcation defined in claim 1, as presented above, is clamped in a detachable way, the profiled balloon consisting of three non-separable parts a distal part, of smaller diameter, a proximal part, of greater diameter, and a medial part having length of 0.5 to 8 mm located between the distal part and the proximal part, position of the medial ring coinciding with the proximal edge of the distal part of the stent clamped on the balloon.

Preferably, a ratio of the distal part diameter to the proximal part diameter of the profiled balloon is within the limits of 1.0:1.1 to 1.0:2.0.

Between the long edges of the distal part of the profiled balloon and the edge of the medial part of the profiled balloon there is an angle θ that lies within the limits of 15° to 65°.

Upon clamping the stent for bifurcation on the profiled balloon in a separable way, a cell having an enlarged surface area of the stent for bifurcation, coincides with the medial part of the profiled balloon.

Method of introducing and positioning the stent for bifurcation by means of an intravascular system including the stent of the invention, is characterized in that a guide wire is introduced to a main branch of a vessel at bifurcation site, after which, a system defined in claim 3, as presented above, is introduced into the bifurcation site, including the stent defined in claim 1, as presented above, a medial ring visible at X-rays signaling a position of the proximal edge of the distal part of the stent clamped on the balloon being precisely positioned at a site, where there is a groin of the vessel, such that the distal part of the stent is situated behind a fork of the artery, in a main branch, whereas the proximal part of the stent is situated before the fork of the artery, and the medial part of the stent, with a cell of the stent having special, enlarged surface area, is located in the lumen of the lateral branch of the vessel, and then liquid under pressure from 6 to 20 atm is introduced to the balloon, the stent is implanted, then, the fluid is removed from the balloon and the system and the guide wire are withdrawn.

On the internal tube of the system for intravascular implantation of the stent for bifurcation, three rings visible at X-rays, are fastened, in such a way, that a first ring coincides with a beginning of long edges of the proximal part of the profiled balloon, a second ring coincides with a beginning of long edges of the distal part of the profiled balloon, whereas a third ring coincides with an ending of long edges of the distal part of the profiled balloon.

The stent for bifurcation is suitably clamped in a detachable way on the profiled balloon.

BRIEF DESCRIPTION OF THE DRAWINGS

The stent for bifurcation and the system for its implantation in an embodiment example is shown on a drawing, in which.

DESCRIPTION OF PREFERRED EMBODIMENTS

A special, profiled structure of the stent for bifurcation allows such positioning of the system for intravascular implantation of the stent for bifurcation during implantation of the stent for bifurcation that the distal part of the stent is positioned behind the fork of the vessel, in a more narrow part of the vessel, the proximal part of the stent for bifurcation is positioned before the fork of the vessel, and the medial part of the stent, with connectors of the stent, forming at the same time the cell of the stent having special, enlarged surface area, being positioned precisely in a lumen of the lateral branch, thereby preventing from blocking blood flow through the lateral branch of the artery.

Two opposite connectors assure that both parts of the stent are kept at a suitable distance from each other, but at the same time the connectors allow, within a defined range, free adjusting to an anatomical shape of vessels. Both parts of the stent upon implantation are supported in an uniform way by the two connectors located symmetrically on two sides of the stent.

Figure 1:
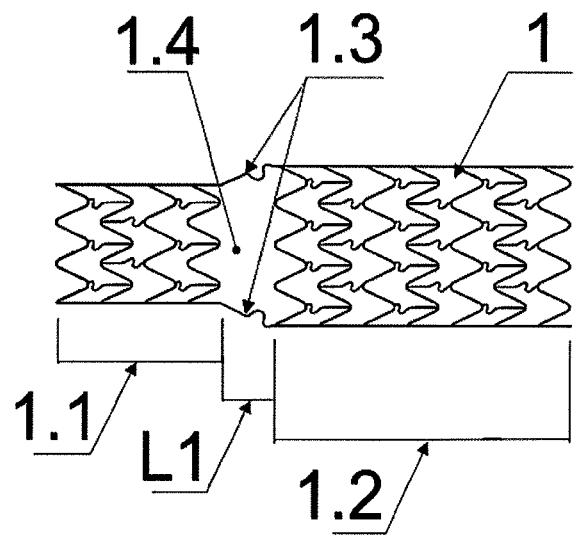
FIG. 1 shows a view of the stent for bifurcation with a visible cell of the stent having enlarged surface area, in FIG. 2 the balloon constituting an element of the system for stent implantation is shown, in FIG. 3—a view of the distal part of the system for intravascular implantation of the stent for bifurcation and its location in a branch of artery, being a site of implantation of the stent is shown, in FIG. 4 the stent located in the vessel at its bifurcation site upon withdrawal of the system, and in FIGS. 5A, 5B, 5C—as a matter of example—positions of the distal part and the proximal of the stent upon its positioning in the vessel are shown.
Figure 2:
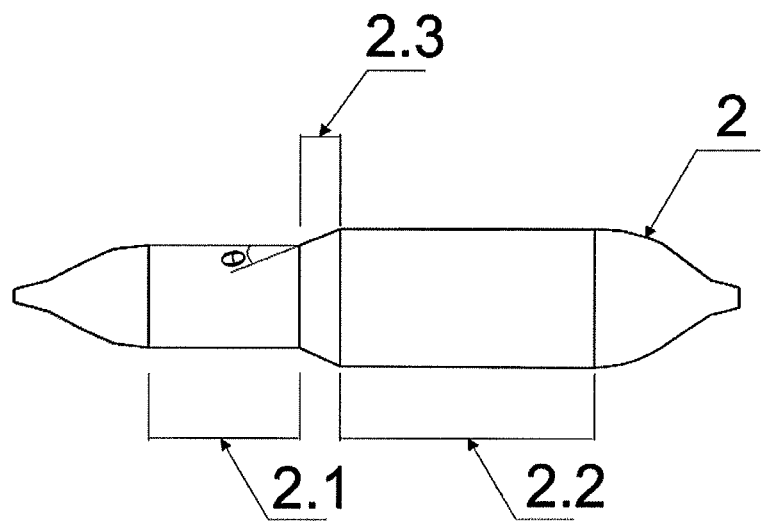
Figure 3:
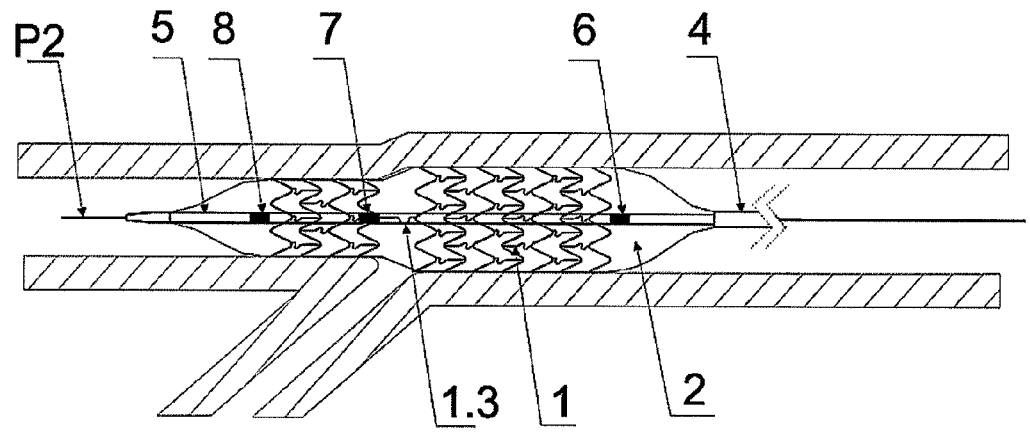
Figure 4:
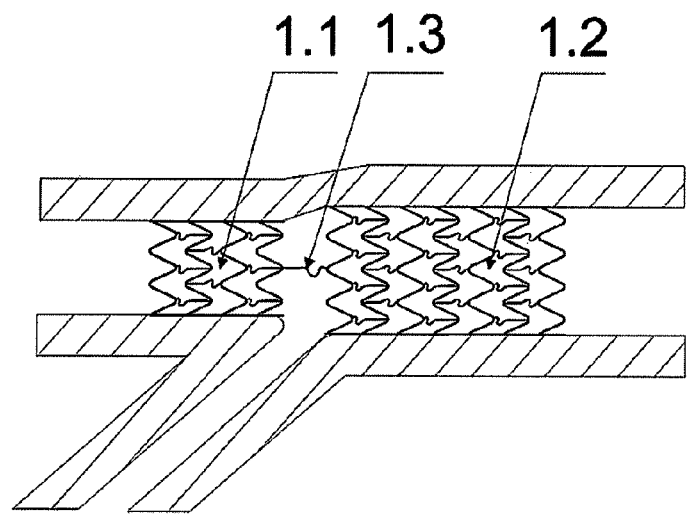
Figure 5A:
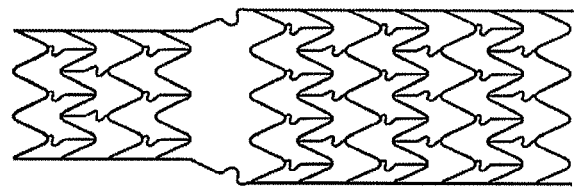
Figure 5B:
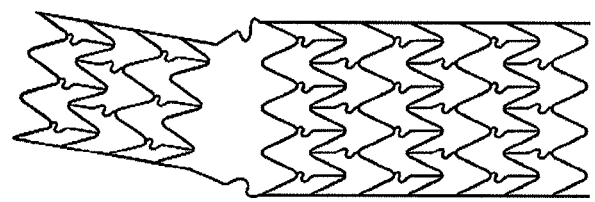
Figure 5C:
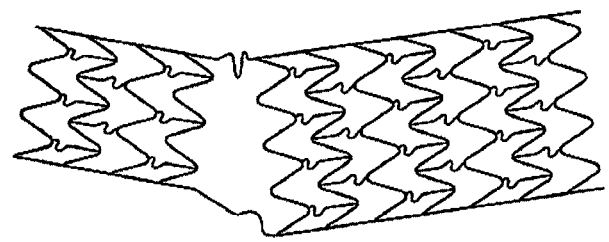

Connectors are located longitudinally with respect to the stent and are curved e.g. have a sinusoidal shape, a wavy shape, a shape of letter "S" or a double "S" shape or an accordion shape or are slightly twisted, like an extended fragment of a helix. Such shapes of connectors cause that—depending on a structure of the vessel, where the stent will be implanted—they may be easily expanded or clamped, so that a primary distance between the proximal part and the distal part of the stent will be increased or decreased. A distance between the parts of the stent upon its implanting at the side of the first connector and at the side of the second connector may be different, as it is shown in FIGS. 5B and 5C. In that case, the parts of the stent are positioned to each other in such a way that there is an angle between them. The connectors also make it possible to carry out a slight shift of the proximal part and the distal part of the stent with respect to the longitudinal axis of the stent. Primarily both parts of the stent are arranged in such a way that their symmetry axes overlap, as it is shown in FIG. 1. No matter how parts of the stent will be arranged with respect to each other upon implanting, the two opposite connectors limit freedom of movement of the stent at its implantation and do not enable unrestricted movement of the distal part and the proximal part of the stent.

Location of a system of three rings (markers) well visible at X-rays on the internal tube provides precise positioning and visibility of the stent for bifurcation during its implantation in vessels. The stent for bifurcation is tightened in a separable way on the profiled balloon in such a way that a cell having an enlarged surface area of the stent for bifurcation coincides with the medial part of the profiled balloon. Marker 7 coincides with the proximal edge of the distal part of the stent clamped on the balloon, and during implantation of the stent, marker 7 must coincide in the vessel with a beginning of the groin of the vessel (carina). A specific shape of the profiled balloon prevents from shifting the groin of the vessel (carina) during implantation of the stent for bifurcation, thus preventing from blocking blood flow through the lateral branch of the artery.

The stent expandable on the balloon of the invention is entirely made of typical, known materials used for such purposes, preferably of stainless steel 316L or alloy L605.

The stent for bifurcation 1 of the invention, consists of two cylindrical segments—of the distal part, of smaller diameter 1.1 and of the proximal part, of greater diameter 1.2, connected by two connectors 1.3 having length L1, forming the cell of the stent having an enlarged surface area 1.4. The distal part of the stent may be longer or shorter than the proximal part of the stent. Both parts of the stent may also be approximately equal to each other. Prior to implantation both parts of the stent are positioned coaxially. The connectors, with which the stent is equipped, are arranged as opposite—i.e. on a circumference of the stent they are located 180° apart. A distance between the proximal part and the distal part of the stent may have length from 0.5 to 8 mm, e.g. from 0.5 to 3 mm or from 2 to 4 mm, or from 3 to 8 mm. Preferably both connectors have equal length. Preferably connectors are not rectilinear but are of a curved shape, e.g. a sinusoidal shape.

The system for intravascular implantation of the stent for bifurcation of the invention in its distal part consists of the profiled balloon 2 fastened to the system in that way that the proximal part 2.2 of the profiled balloon 2 is fastened to the external surface of the external tube 4 of the system, and the distal part 2.1 of the profiled balloon 2 is fastened to the external surface of the internal tube 5 of the system. The profiled balloon 2 consists of three non-separable parts: the distal part, of smaller diameter 2.1, the proximal part, of greater diameter 2.2, and the medial part 2.3 of a defined length, located between the distal part 2.1 and the proximal part 2.2. The distal part of the balloon may be longer or shorter than the proximal part of the balloon. Both parts of the balloon may also be approximately equal. The medial part of the balloon is adjusted to a distance between the distal part and the proximal part of the stent and may have length from 0.5 to 8 mm, for example from 0.5 to 3 mm or from 2 to 4 mm, or from 3 to 8 mm.

Between long edges of the distal part 2.1 and an edge of the medial part 2.3 of the profiled balloon 2 there is an angle Θ. The stent for bifurcation 1 is clamped in a separable way on the profiled balloon 2 in such a way that the cell of the stent having an enlarged surface area 1.4 of the stent for bifurcation 1 coincides with the medial part 2.3 of the profiled balloon 2, the distal part of the stent 1.1 is mounted on the distal part of the balloon 2.1 and the proximal part of the stent 1.2 is mounted on the proximal part of the balloon 2.2.

On the internal tube 5 of the system for intravascular implantation of the stent for bifurcation at least one ring 7 is fastened, preferably three rings 6, 7, 8, visible at X-rays, in such a way, that the ring 6 coincides with a beginning of long edges of the proximal part 2.2 of the profiled balloon 2, the ring 7 coincides with a beginning of long edges of the distal part 2.1 of the profiled balloon 2, and the ring 8 coincides with an ending of long edges of the distal part 2.1 of the profiled balloon 2. The stent is tightened in a separable way on the balloon of the system in such a way that the ring 6 coincides with the proximal edge of the stent 1, the ring 8 coincides with the distal edge of the stent 1, and the ring 7 coincides with the proximal edge of the distal part 1.1 of the stent, in other words the ring 7 coincides with that edge of the distal part of the stent, which is situated at the side of the cell of the stent having an enlarged surface area 1.4.

The system for intravascular implantation of the stent of the invention is introduced into body in that way, that the guide wire P2 is delivered to the bifurcation site that is positioned in the main branch of the artery.

Then, the system for intravascular implantation of a stent of the invention is introduced on the guide wire P2.

The internal tube 5 of the system for intravascular implantation of the stent is put onto the guide wire P2.

Then, while shifting the entire system for intravascular implantation of the stent on the guide wire P2, controlling at the same time position of the three rings 6, 7, 8 by X-rays, the stent for bifurcation 1 with the profiled balloon 2 is very precisely positioned at the bifurcation site: the system is introduced on the guide wire P2 into the main branch of the artery, so that the ring 7 would be at the same height, where the groin of the vessel (carina) is situated. By means of control of position of the marker 7 it is possible to position proximal edges of the distal part of the stent 1 precisely in one line with the groin of the vessel (carina).

Such introduction of the system for intravascular implantation of the stent for bifurcation results in that the distal part 1.1 of the stent for bifurcation is situated behind the fork of the artery, in the main branch, the proximal part 1.2 of the stent for bifurcation is situated before the fork of the artery, and the medial part of the stent, with the cell of the stent having a special, enlarged surface area 1.4, is positioned in a lumen of the lateral branch.

Then, a fluid under pressure of 6 to 20 atm is introduced to the profiled balloon 2, which causes expanding of the profiled balloon 2, thus opening the stent for bifurcation 1. The open stent for bifurcation 1 widens lumen of the vessel, thus eliminating contraction.

Upon total opening of the stent for bifurcation 1, its medial part, with the cell of the stent having a special, enlarged surface area 1.4, is positioned precisely in a lumen of the lateral branch, which allows free blood flow through the lateral branch of the artery.

Then, the fluid is removed from the profiled balloon 2, the whole system with the empty profiled balloon 2 is withdrawn from blood circulation system. At the end, the guide wire P2 is withdrawn. The open stent for bifurcation 1 remains at the site, where there was contraction of the artery, thus causing its permanent widening.

What is claimed is:

1. A system for intravascular implantation of a stent for bifurcation, the system comprising:
   a stent, an external tube, an internal tube marked with a ring visible on an X-ray image, and a profiled balloon;
   the profiled balloon comprises a proximal part fastened to an external surface of the external tube, and a distal part fastened to an external surface of the internal tube;
   the stent comprising a distal cylindrical part, a proximal cylindrical part of greater diameter than the distal part, and two longitudinal connectors connecting the distal part and the proximal part of the stent;
   the two longitudinal connectors arranged on opposite sides of the stent, having lengths of 0.5 to 8 mm, and forming a cell of the stent having a surface area enlarged compared with the surface area of the distal cylindrical part;
   the two longitudinal connectors having a curvilinear shape and clamped on the profiled balloon in a detachable way;
   the profiled balloon comprising the distal part, the proximal part of greater diameter than the distal part, and a medial part having length from 0.5 to 8 mm and located between the distal part and the proximal part,
   wherein the distal part, the proximal part and the medial part of the profiled balloon are non-separable; and
   a position of the ring coinciding with the proximal edge of the distal part of the stent clamped on the balloon,
   wherein upon clamping the stent in a separable way on the profiled balloon, the cell encompassing the medial part of the profiled balloon.

2. A system of claim 1, wherein a ratio of the distal part diameter to the proximal part diameter of the profiled balloon is within the limits of 1.0:1.1 to 1.0:2.0.

3. A system of claim 1, wherein between long edges of the distal part of the profiled balloon and an edge of the medial part of the profiled balloon there is an angle that lies within the limits of 15° to 65°.

4. The system of claim 1, wherein the proximal part of the stent is configured to be positioned before, in a blood circulating direction, a fork of an implantation artery and the distal part of the stent is configured to be positioned behind, in a blood circulating direction, the fork of the implantation artery.

5. The system of claim 1, wherein the distal cylindrical part of the stent is configured to be implanted in a main blood vessel, and a proximal cylindrical part of the stent is configured to be implanted in the main blood vessel.

6. A system for intravascular implantation of a stent for bifurcation, the system comprising:
   a stent, an external tube, an internal tube, and a profiled balloon;
   the profiled balloon comprises a proximal part fastened to an external surface of the external tube, and a distal part fastened to an external surface of the internal tube;
   the stent comprising a distal cylindrical part, a proximal cylindrical part of greater diameter than the distal part, and exactly two longitudinal connectors connecting the distal part and the proximal part of the stent;
   the two longitudinal connectors arranged on opposite sides of the stent and forming a cell of the stent;
   the two longitudinal connectors having a curvilinear shape and clamped on the profiled balloon in a detachable way; and
   the profiled balloon comprising the distal part, the proximal part of greater diameter than the distal part, and a medial part located between the distal part and the proximal part,
   wherein the distal part, the proximal part and the medial part of the profiled balloon are non-separable; and wherein upon clamping the stent in a separable way on the profiled balloon, the cell encompassing the medial part of the profiled balloon.

7. A system of claim 6, wherein a ratio of the distal part diameter to the proximal part diameter of the profiled balloon is within the limits of 1.0:1.1 to 1.0:2.0.

8. A system of claim 6, wherein between long edges of the distal part of the profiled balloon and an edge of the medial part of the profiled balloon there is an angle that lies within the limits of 15° to 65°.

9. The system of claim 6, wherein the proximal part of the stent is configured to be positioned before, in a blood circulating direction, a fork of an implantation artery and the distal part of the stent is configured to be positioned behind, in a blood circulating direction, the fork of the implantation artery.

10. The system of claim 6, wherein the internal tube is marked with a ring visible on an X-ray image, and the position of the ring coincides with a proximal edge of the distal part of the stent.

11. The system of claim 6, wherein the two longitudinal connectors have lengths of 0.5 to 8 mm, and the cell of the stent has an enlarged surface area.

12. A system for intravascular implantation of a stent for bifurcation, the system comprising:
   a stent, an external tube, an internal tube, and a profiled balloon;
   the profiled balloon comprises a proximal part fastened to an external surface of the external tube, and a distal part fastened to an external surface of the internal tube;
   the stent comprising a distal cylindrical part, a proximal cylindrical part of greater diameter than the distal part, and exactly two longitudinal connectors connecting the distal part and the proximal part of the stent;
   the two longitudinal connectors arranged on opposite sides of the stent, and forming a cell of the stent having an enlarged surface area;
   the two longitudinal connectors having a curvilinear shape and clamped on the profiled balloon in a detachable way; and
   the profiled balloon comprising the distal part, the proximal part of greater diameter than the distal part, and a medial part and located between the distal part and the proximal part,
   wherein the distal part, the proximal part and the medial part of the profiled balloon are non-separable;
   wherein upon clamping the stent in a separable way on the profiled balloon, the cell encompassing the medial part of the profiled balloon,
   wherein the stent is configured to be supported by and positioned in a single implantation artery.

13. A system of claim 12, wherein a ratio of the distal part diameter to the proximal part diameter of the profiled balloon is within the limits of 1.0:1.1 to 1.0:2.0.

14. A system of claim 12, wherein between long edges of the distal part of the profiled balloon and an edge of the medial part of the profiled balloon there is an angle that lies within the limits of 15° to 65°.

15. The system of claim 12, wherein the proximal part of the stent is configured to be positioned before, in a blood circulating direction, a fork of an implantation artery and the distal part of the stent is configured to be positioned behind, in a blood circulating direction, the fork of the implantation artery.

16. The system of claim 12, wherein the internal tube is marked with a ring visible on an X-ray image, and the position of the ring coincides with a proximal edge of the distal part of the stent.

17. The system of claim 12, wherein the two longitudinal connectors have lengths of 0.5 to 8 mm, and the cell of the stent has an enlarged surface area.

18. The system of claim 12, wherein the cell has a surface area enlarged compared with the surface area of the distal cylindrical part.

19. The system of claim 12, wherein the stent comprises exactly two connectors connecting the distal part and the proximal part.

20. The system of claim 12, wherein the cell has a surface area enlarged compared with the surface area of the distal cylindrical part, wherein the stent comprises exactly two connectors connecting the distal part and the proximal part.

* * * * *